US00PP33217P2

(12) United States Plant Patent
Van Swieten

(10) Patent No.: US PP33,217 P2
(45) Date of Patent: Jun. 29, 2021

(54) ***PHALAENOPSIS* ORCHID PLANT NAMED 'PHALHASVEL'**

(50) Latin Name: ***Phalaenopsis* hybrid**
Varietal Denomination: PHALHASVEL

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,419

(22) Filed: Jan. 27, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'PHALHASVEL', QZ PBR 2019/2388, filed Sep. 23, 2019.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALHASVEL', particularly characterized by light greenish-yellow, shaded, and striped flowers with reddish-purple lips, no whiskers, a convex flower shape in lateral view, and is propagated by meristem tissue culture, is disclosed.

3 Drawing Sheets

Genus and species: *Phalaenopsis* hybrid.
Variety denomination: 'PHALHASVEL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHASVEL'.

The new *Phalaenopsis* plant is a product of a planned breeding program conducted by the inventor in Bleiswijk, the Netherlands. The objective of this breeding program was to create a new, short *Phalaenopsis* plant with light greenish-yellow, shaded, and striped flowers with reddish-purple lips, suitable for potted plant production.

The new *Phalaenopsis* plant 'PHALHASVEL' is a result of cross-pollination made by the inventor in September 2011 in Bleiswijk, the Netherlands, of the proprietary female, or seed parent, *Phalaenopsis* hybrid '21864-012' (unpatented) with the proprietary male, or pollen parent, *Phalaenopsis* hybrid '20413-03' (unpatented).

The new *Phalaenopsis* was selected by the inventor as a single plant within the progeny of the stated cross-pollination in a controlled greenhouse in Bleiswijk, the Netherlands, in September 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 23, 2019

(Application no. 2019/2388), by Applicant who obtained the subject matter disclosed directly from the inventor. 'PHALHASVEL' has not been made publicly available or sold anywhere in the world prior to the effective filing date of this application with the exception of sales or disclosures made one year or less before the effective filing date of this claimed invention by Applicant who obtained 'PHALHASVEL' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHASVEL' as a new and distinct variety of *Phalaenopsis* plant:

1) Light greenish-yellow, shaded, and striped flowers with reddish-purple lips;
2) Whiskers are absent; and
3) Flower shape in lateral view is convex.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in November 2020. Colors in the photographs may differ from the color values cited in the detailed botanical description, which accurately describe the actual colors of the new variety.

DESCRIPTION OF THE NEW VARIETY

Figure 1:
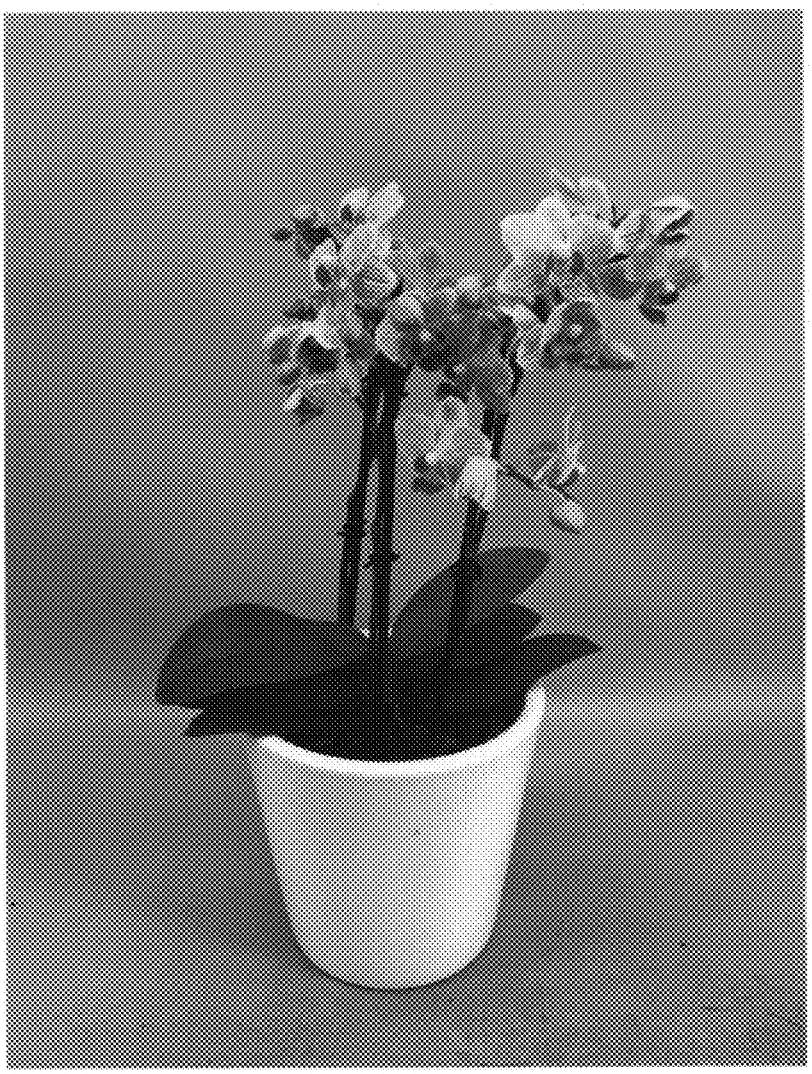
FIG. 1 shows the overall plant habit, including blooms, buds, and foliage of 'PHALHASVEL'.
Figure 2:
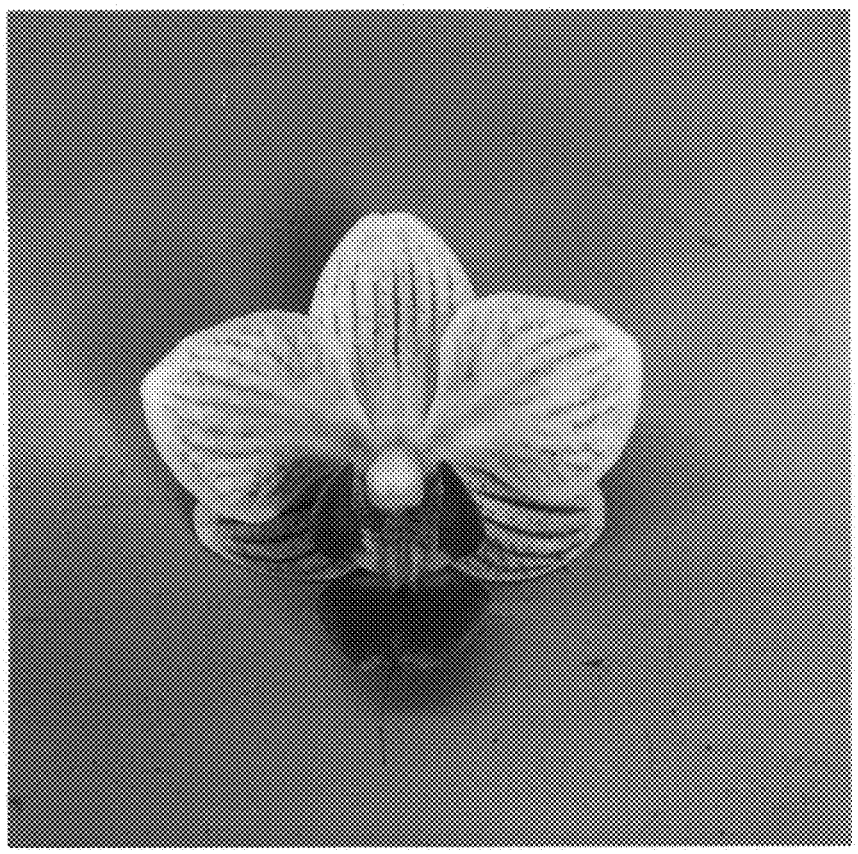
FIG. 2 shows a close-up of a flower of 'PHALHASVEL'.
Figure 3:
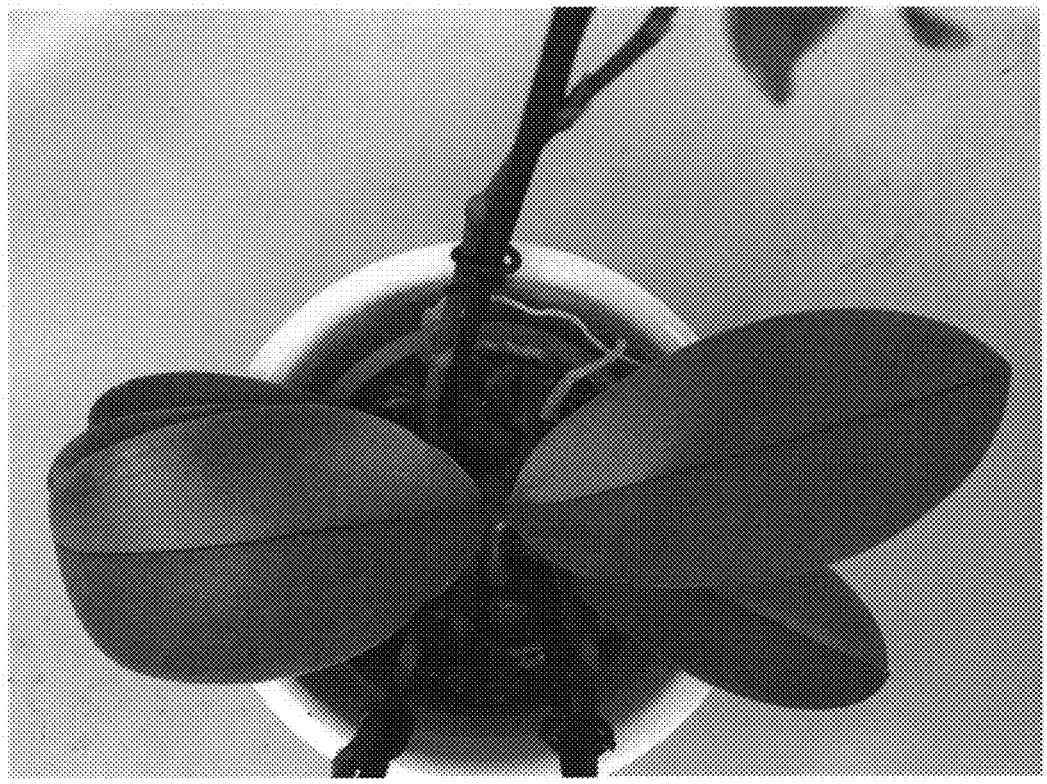
FIG. 3 shows an overhead view of the leaves of 'PHALHASVEL'.

The following detailed description sets forth the distinctive characteristics of 'PHALHASVEL'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHASVEL'.

Parentage:

*Female parent*.—*Phalaenopsis* cultivar '21864-012' (unpatented).

*Male parent*.—*Phalaenopsis* cultivar '20413-03' (unpatented).

Propagation:

*Type*.—Meristem tissue culture.

Roots:

*Root description*.—Greyed-green (something between RHS 190B and 190C) colored roots with branching lateral roots having yellow-green (RHS 145A) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height (from soil level to top of inflorescence)*.—Approximately 19.0 cm to 24.0 cm.

*Width (measured from leaf tips)*.—About 21.0 cm to 23.0 cm.

*Vigor*.—Strong.

Leaves:

*Mature leaves*.—Quantity per plant: 10 to 12 leaves are produced before flowering. Length (fully expanded): 9.0 cm to 11.0 cm. Width: 5.0 cm to 6.0 cm. Position of the broadest part of the leaf: At the middle. Shape: Oblong. Base shape: Moderately elongated. Apex: Unequal obtuse. Leaf blade angle with the petiole (measured from the horizontal position): Between 5 degrees and 20 degrees. Leaf margin: Entire. Color: Upper surface: RHS 146A. Lower surface: RHS 146B with a hint of diluting brown (RHS 200C) toward the margin. Texture (both upper and lower surfaces): Smooth. Thickness: 1.7 mm to 2.2 mm. Variegation: Absent. Venation: Pattern: Parallel. Color of the midvein: Upper surface: RHS 146A. Lower surface: RHS 146B with a touch of reddish-brown (RHS 200B).

Peduncle:

*Quantity per plant*.—1 to 3.

*Number of flowers per peduncle*.—10 to 17.

*Length*.—19.0 cm to 24.0 cm.

*Diameter*.—3.7 mm to 4.2 mm.

*Strength*.—Strong.

*Aspect*.—Upright to slightly pendent.

*Texture*.—Smooth.

*Color*.—Mix of yellow-green (RHS 146C) and dark red-brown (something in between RHS 187B and 200B).

*Internode length*.—1.5 cm to 2.5 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 120.0 mm to 170.0 mm.

*Flowering time*.—First flowers can be expected 10 to 11 months after planting in a 12-cm pot.

*Flower*.—Height: 43.0 mm to 48.0 mm. Diameter: 44.0 mm to 49.0 mm. Depth of lip: 15.0 mm to 17.0 mm.

*Flower longevity*.—On the plant: 13 to 15 weeks.

*Flower shape*.—Convex.

*Fragrance*.—Absent.

*Flower bud*.—Average size: Medium. Length: 15.0 mm to 17.0 mm. Width: 13.0 mm to 15.0 mm. Shape: Egg shaped. Color: Yellow-green (something in between RHS 154C and 151B) at the base with a touch of purplish-red (RHS 185C).

*Petals*.—Arrangement: Open/free. Shape: Semi-circular. Apex: Obtuse asymmetric. Margin: Weakly undulated. Length (from base to tip): 16.0 mm to 18.0 mm. Width: 16.0 mm to 18.0 mm. Position of the broadest part of the petal: Toward the base. Color (when fully opened): Upper surface: Basic color: Light greenish-yellow (RHS 4B). Over color: Shaded (RHS N75A) at the base; purplish-red stripes (something in between RHS 72A and 72B). Lower surface: Basic color: Light greenish-yellow (RHS 4C). Over color: Touch of very light purple (RHS 76C) at the base and light purple midvein (RHS 76A). Number of spots and stripes on the petals (upper surface): Medium stripes. Color of spots and stripes on the petals (upper surface): Something in between RHS 72A and 72B. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 18.0 mm to 20.0 mm. Width: 14.0 mm to 16.0 mm. Position of the broadest part of the dorsal sepals: At the middle. Color (when fully opened): Upper surface: Basic color: Light greenish-yellow (RHS 4B). Over color: Shaded (RHS N75A) at the base; purplish-red stripes (RHS 71A). Lower surface: Basic color: Greenish-yellow (RHS 1B). Over color: Diluting light purple stripes (RHS 76A). Number of spots and stripes on the dorsal sepals (upper surface): Medium stripes. Color of spots and stripes on the dorsal sepals (upper surface): RHS 71A. Density of netting of the dorsal sepals (upper surface): None. Color of the netting: Not applicable.

*Lateral sepals*.—Shape: Ovate. Apex: Obtuse symmetric. Margin: Entire. Length (from base to tip): 19.0 mm to 21.0 mm. Width: 14.0 mm to 16.0 mm. Position of the broadest part of the lateral sepals: At the base. Color (when fully opened): Upper surface: Basic color: Light greenish-yellow (RHS 4B). Over color: Small dots (RHS 71A) and shaded (RHS N75A) at the base; stripes (RHS 71A). Lower surface: Basic color: Light greenish-yellow (something in between RHS 4B and 4C). Over color: Light yellow-green (RHS 145C); few purplish-pink stripes and midvein (RHS N78C). Number of spots, dots, and stripes on the lateral sepals (upper surface): Medium stripes and few small dots at the base. Color of spots, dots, and stripes on the lateral sepals (upper surface): RHS 71A. Density of netting of the lateral sepals (upper surface): None. Color of the netting (upper surface): Not applicable.

*Labellum* (*lip*).—Whiskers: Absent. Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 11.0 mm to 13.0 mm. Width: 5.0 mm to 7.0 mm. Color: Upper surface: Light yellow-green (RHS 155A) at the base with a touch of yellow (RHS 12B); red (something in between RHS 185A and 185B) and reddish-purple (RHS N78A) toward the tip. Lower surface: Light yellow-green (RHS 155A) at the base; touch of red (RHS 181A) at margin on one side and reddish-purple (something in between RHS N78B and N78C) toward the tip. Number of spots, dots, and stripes on the lateral lobe: Few very small dots at the base. Color of spots, dots, and stripes on the lateral lobe: RHS 184A. Density of netting of the lateral lobe: None. Color of the netting: Not applicable.

*Apical lobe*.—Shape: Ovate. Margin: Entire. Length: 13.0 mm to 15.0 mm. Width: 12.0 mm to 14.0 mm. Color: Upper surface: Yellow (RHS 12A) at the base; red (something in between RHS 185A and 185B) and reddish-purple (RHS N78A) with a touch of white (RHS NN155C) toward the tip. Lower surface: Touch of yellow (RHS 12A) at the margin from base toward wings; yellowish-white (RHS 155D) at the middle; light reddish-purple margin (RHS N78D) toward the tip. Number of spots and stripes on the apical lobe: None. Color of spots and stripes on the apical lobe: Not applicable. Density of netting of the apical lobe: None. Color of the netting: Not applicable.

*Callus*.—Average size: Small. Height: 3.0 mm to 4.0 mm. Length: 2.0 mm to 3.0 mm. Width: 2.0 mm to 3.0 mm. Color: Yellow (RHS 12A) at the top; light greenish-yellow (RHS 4B) on sides and purplish-red dots (RHS 187D).

Reproductive organs:

*Column*.—Length: 7.0 mm to 8.0 mm. Diameter: 3.7 mm to 4.2 mm. Color: Purplish-pink (RHS N78C) at the base with white tip (RHS NN155C).

*Pollinia*.—Quantity: 2. Diameter: 0.8 mm to 1.0 mm. Color: Orange-yellow (RHS 17A).

*Ovary*.—Length: 8.0 mm to 10.0 mm. Diameter: 1.4 mm to 1.5 mm.

*Pedicel*.—Length: 24.0 mm to 26.0 mm. Diameter: 1.5 mm to 1.6 mm. Texture: Smooth. Color: Light yellow-green (RHS 145C) at the base and lighter yellow-green (something in between RHS 145D and 150D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHASVEL' differs from the female parent plant '21864-012' (unpatented), in that 'PHALHASVEL' has flowers with a shaded and striped pattern, whereas '21864-012' has flowers with a spotted pattern. Additionally, 'PHALHASVEL' has smaller flowers than '21864-012'.

'PHALHASVEL' differs from the male parent plant '20413-03' (unpatented) in that 'PHALHASVEL' has flowers with a main color of light greenish-yellow and no whiskers, whereas '20413-03' has flowers with a main color of reddish-purple and whiskers.

'PHALHASVEL' is most similar to the commercial *Phalaenopsis* plants named 'PHALYPBE' (U.S. Plant patent application Ser. No. 16/923,579) and 'PHALCOFALI' (unpatented). 'PHALHASVEL' differs from the commercial variety 'PHALYPBE' in that 'PHALHASVEL' has ovate apical lobes, obtuse lateral sepal apexes, and no whiskers, whereas 'PHALYPBE' has rhombic apical lobes, emarginated lateral sepal apexes, and whiskers. Additionally, 'PHALHASVEL' has shorter leaves than 'PHALYPBE'.

'PHALHASVEL' differs from the commercial variety 'PHALCOFALI' in that 'PHALHASVEL' has emarginated dorsal sepal apexes, whereas 'PHALCOFALI' has rounded dorsal sepal apexes. Additionally, 'PHALHASVEL' has smaller flowers and shorter leaves than 'PHALCOFALI'.

I claim:

1. A new and distinct variety of *Phalaenopsis* plant named 'PHALHASVEL', substantially as described and illustrated herein.

* * * * *